United States Patent
Wan et al.

(10) Patent No.: US 8,956,638 B2
(45) Date of Patent: Feb. 17, 2015

(54) BIOCOMPATIBLE POLY (AMIC ACID) AND METHOD OF PREPARATION THEREOF

(75) Inventors: Wankei Wan, London (CA); Donna Padavan, London (CA)

(73) Assignee: Axcelon Biopolymers Corporation, London, ON (CA)

( * ) Notice: Subject to any disclaimer, the term of this patent is extended or adjusted under 35 U.S.C. 154(b) by 318 days.

(21) Appl. No.: 13/639,826

(22) PCT Filed: Apr. 8, 2011

(86) PCT No.: PCT/CA2011/050189
§ 371 (c)(1), (2), (4) Date: Feb. 20, 2013

(87) PCT Pub. No.: WO2011/123957
PCT Pub. Date: Oct. 13, 2011

(65) Prior Publication Data
US 2013/0143325 A1    Jun. 6, 2013

Related U.S. Application Data

(60) Provisional application No. 61/322,178, filed on Apr. 8, 2010.

(51) Int. Cl.
| | |
|---|---|
| *A61L 27/34* | (2006.01) |
| *A61K 47/34* | (2006.01) |
| *A61L 31/10* | (2006.01) |
| *C08G 69/26* | (2006.01) |
| *C08G 69/28* | (2006.01) |
| *A61L 27/18* | (2006.01) |
| *A61L 27/54* | (2006.01) |
| *A61L 31/06* | (2006.01) |
| *A61L 31/16* | (2006.01) |
| *C12N 5/071* | (2010.01) |
| *C12N 11/08* | (2006.01) |

(52) U.S. Cl.
CPC ............ *A61L 27/34* (2013.01); *A61K 47/34* (2013.01); *A61L 27/18* (2013.01); *A61L 27/54* (2013.01); *A61L 31/06* (2013.01); *A61L 31/10* (2013.01); *A61L 31/16* (2013.01); *C12N 5/069* (2013.01); *C12N 11/08* (2013.01)
USPC ........... 424/422; 424/423; 435/396; 523/113; 525/436; 525/54.1; 514/1.1; 514/23; 514/53; 514/54; 514/788; 514/772.3; 524/878; 528/422

(58) Field of Classification Search
CPC ..... A61K 31/70; A61K 31/715; A61K 38/02; A61K 47/34; A61K 47/48238; A61L 27/18; A61L 27/34; A61L 31/041; A61L 31/06; C08L 77/00

USPC .................. 424/422, 423; 435/396; 523/113; 525/436, 54.1; 514/1.1, 23, 53, 54, 514/788, 772.3; 524/878; 528/422

See application file for complete search history.

(56) References Cited

U.S. PATENT DOCUMENTS

| | | |
|---|---|---|
| 5,248,760 A | 9/1993 | DuBois et al. |
| 2008/0262191 A1 | 10/2008 | Mizori |
| 2010/0266814 A1 | 10/2010 | Bury et al. |

OTHER PUBLICATIONS

Allcock et al. (Contemporary Polymer Chemistry, 3rd Edition, Published 2003, pp. 2-4).*
International Search Report. PCT/CA2011/050189. Mailed Sep. 7, 2011. Completion date Aug. 18, 2011.
R. Langer and D. A. Tirrell, Nature 428, 487 (2004).
X. Jiang, E. B. Vogel, M. R. Smith and G. L. Baker, Macromolecules, 41, 1937 (2008).
A. A. Ignatius and L. E. Claes, Biomaterials 17, 831 (1996).
M. Hakkarainen, A. Hoglund, K. Odelius and A. C. Albertsson. Journal of the American Chemical Society 129, 6308 (2007).
D. E. Johnston, D.R. Boughner, M. Cimini and K. A. Rogers. J Biomed Mater Res A, 78A, 383 (2006).
K. A. Rogers, P. Boden, V. I. Kalnins and A. I. Gotlieb, Cell and Tissue Research, 243, 223 (1986).
Millipore, WST-1 Cell Proliferation Assay, http://www.millipore.com/cellbiology/cb3/wst-1. Aug. 2009.
D. L. Pavia, Introduction to spectorscopy, Brooks/Cole, Cengage Learning, Belmont, CA 2009.
M. B. Inoue et al., Binuclear Copper(II) Chelates of Amide-Based Cyclophanes. Inorg. Chem. 37, 4070-4075. (1998).
D. T. Padavan et al., Synthesis and In Vitro Biocompatibility Assessment of a Poly(amic acid) Derived from Ethylenediaminetetraacetic Dianhydride. Journal of tBiomaterials Science, 22, 683-700. (2011).
D. T. Padavan et al. Synthesis and characterization of a novel versatile poly(amic acid) derived from Ethylenediaminetetraacetic Dianhydride, Materials Chemistry and Physics. Elsevier. 124, (2010).

* cited by examiner

Primary Examiner — Richard Schnizer
Assistant Examiner — Alma Pipic
(74) Attorney, Agent, or Firm — Hill & Schumacher; Lynn C. Schumacher; Stephen W. Leonard

(57) ABSTRACT

A method is provided for the preparation of a poly(amic acid) in which ring opening polymerization is employed to react the monomers ethylenediaminetetraacetic dianhydride and paraphenylenediamine in an aprotic solvent. The resulting poly (amic acid) composition is suitable as a biocompatible material, such as a biomedical implant, implant coating material, tissue scaffold material, controlled release drug delivery vehicle, and cellular growth substrate.

28 Claims, 12 Drawing Sheets

BIOCOMPATIBLE POLY (AMIC ACID) AND METHOD OF PREPARATION THEREOF

CROSS-REFERENCE TO RELATED APPLICATION

This application is a National Phase application claiming the benefit of PCT/CA2011/050189 filed on Apr. 8, 2011 in English, which further claims priority to U.S. Provisional Application No. 61/322,178, titled "BIOCOMPATIBLE POLY(AMIC ACID) AND METHOD OF PREPARATION THEREOF" and filed on Apr. 8, 2010, the entire contents of which are incorporated herein by reference.

FIELD OF THE INVENTION

This invention relates to poly(amic acids) and their methods of preparation. More particularly, this invention relates to biocompatible poly(amic acids) and biomedical devices and compositions comprising biocompatible poly(amic acids).

BACKGROUND OF THE INVENTION

The potential biomedical applications of new synthetic polymers continue to increase in both number and complexity. Substantial impact on patient management has already been achieved with a variety of devices such as controlled release delivery systems (as found in coronary artery stents) or in polymer/cell combinations as exemplified by artificial skin used to treat burn patients [1].

Perhaps the most popular class of synthetic biocompatible polymers currently used for medical applications are polyesters. Although widely used, polyester applications have been limited by their hydrophobicity and, as a result, their usefulness has been hindered in aqueous environments. Tailoring the polymer backbone is also difficult since pendant functional groups are lacking, restricting the covalent attachment of bioactive molecules [2]. For degradable polyesters, the nature of the degradation products has also raised concerns about pH fluctuations and its effect on the local tissue environment [3, 4].

SUMMARY OF THE INVENTION

In a first aspect, there is provided a poly(amic acid) polymer of the following formula:

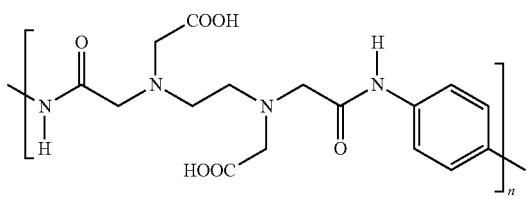

where n is an integer.

The polymer may further comprise a conjugated bioactive moiety, wherein the bioactive moiety is conjugated to one or more of an amide group and a carboxylic group, and where the bioactive moiety may be selected from the group consisting of drugs, peptides, sugars, and cell-specific ligands.

In another aspect, there is provided a biomedical implant comprising: a substrate; and a biocompatible layer coating a surface of the substrate; wherein the biocompatible layer comprises the aforementioned poly(amic acid).

In another aspect, there is provided a biomedical implant comprising the aforementioned biocompatible poly(amic acid). In yet another aspect, there is provided a tissue engineering scaffold comprising the aforementioned biocompatible poly(amic acid). In another aspect, there is provided a controlled release drug delivery vehicle comprising the aforementioned biocompatible poly(amic acid). In another aspect, there is provided a cellular growth substrate material comprising the aforementioned biocompatible poly(amic acid).

In yet another aspect, there is provided a process for preparing a poly(amic acid) comprising the steps of: forming a solution of comprising a quantity of ethylenediaminetetraacetic dianhydride in an aprotic solvent; adding to the solution a quantity of paraphenylenediamine, wherein a molar quantity of the paraphenylenediamine is approximately equal to a molar quantity of the ethylenediaminetetraacetic dianhydride; and reacting the ethylenediaminetetraacetic dianhydride with the paraphenylenediamine to form a polymer solution of poly(amic acid).

The step of reacting the ethylenediaminetetraacetic dianhydride with the paraphenylenediamine to form a polymer solution of poly(amic acid) may be performed while maintaining a temperature of the solution for a selected time interval, and the temperature may be maintained within a range of approximately 20 degrees Celsius to 45 degrees Celsius. The step of reacting the ethylenediaminetetraacetic dianhydride with the paraphenylenediamine to form a polymer solution of poly(amic acid) may be performed in a substantially inert atmosphere.

The aprotic solvent may be selected from the group consisting of N-methyl-2-pyrrolidone (NMP), N,N dimethylformamide (DMF), dimethyl sulfoxide (DMSO) and N,N-dimethylacetamide (DMAc).

The process may further comprise the step of extracting the poly(amic acid) from the polymer solution. The step of extracting the poly(amic acid) may comprise precipitating the poly(amic acid) from the polymer solution and filtering the solution to obtain the poly(amic acid), or may comprise performing a solvent evaporation step. The process may further comprise the steps of: forming a casting solution by dissolving the extracted poly(amic acid) in a solvent; casting the poly(amic acid) onto a substrate; and drying the poly(amic acid) to obtain a solid. The solid may optionally be stored in an environment suitable for removal of residual gases, and may further be thermally incubated for a pre-defined time interval at a temperature suitable for removal of solvent remaining in the solid.

The substrate may comprise a mold, and wherein the process further comprises the step of separating the solid from the mold.

The substrate may comprise a surface of a biomedical implant, and wherein the solid comprises a poly(amic acid) layer coated onto the biomedical implant. The biomedical implant may be a coronary stent. The biomedical implant may comprise a tissue engineering scaffold, and the process may further comprise the steps of: seeding the poly(amic acid) layer with adherent cells; and culturing the adherent cells. After having implanted the biomedical implant, the process may further comprise the step of enzymatically degrading the poly(amic acid).

The process may further comprise the step of conjugating a bioactive moiety to one or more of an amide group and a carboxylic group of the poly(amic acid), where the step of conjugating the bioactive moiety may be performed prior to extracting the poly(amic acid).

In another aspect, there is provided a poly(amic acid) polymer prepared by the steps comprising: forming a solution of comprising a quantity of ethylenediaminetetraacetic dianhydride in an aprotic solvent; adding to the solution a quantity of paraphenylenediamine, wherein a molar quantity of the paraphenylenediamine is approximately equal to a molar quantity of the ethylenediaminetetraacetic dianhydride; reacting the ethylenediaminetetraacetic dianhydride with the paraphenylenediamine to form a polymer solution of poly(amic acid).

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which.

DETAILED DESCRIPTION OF THE INVENTION

As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to a method of poly(amic acid) polymer synthesis using a monomers comprising ethylenediaminetetraacetic dianhydride and paraphenylenediamine.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

As used herein, the terms "about" and "approximately, when used in conjunction with ranges of dimensions of particles, compositions of mixtures or other physical properties or characteristics, is meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present invention.

As used herein, the term "exemplary" means "serving as an example, instance, or illustration," and should not necessarily be construed as preferred or advantageous over other configurations disclosed herein.

In one embodiment, a method is provided wherein a poly(amic acid) polymer comprising amide and acid functional groups is synthesized via ring opening polymerization using an aliphatic dianhydride monomer and a diamine monomer in an aprotic solvent. Preferably, the aliphatic dianhydride monomer comprises ethylenediaminetetraacetic dianhydride. The diamine monomer may comprise an aromatic, aliphatic, or alicyclic diamine, and more preferably comprises paraphenylenediamine. Various aprotic solvents may be employed, and in a non-limiting embodiment, the aprotic solvent is selected from the group consisting of N-methyl-2-pyrrolidone (NMP), N,N dimethylformamide (DMF), dimethyl sulfoxide (DMSO) and N,N-dimethylacetamide (DMAc).

Figure 1:
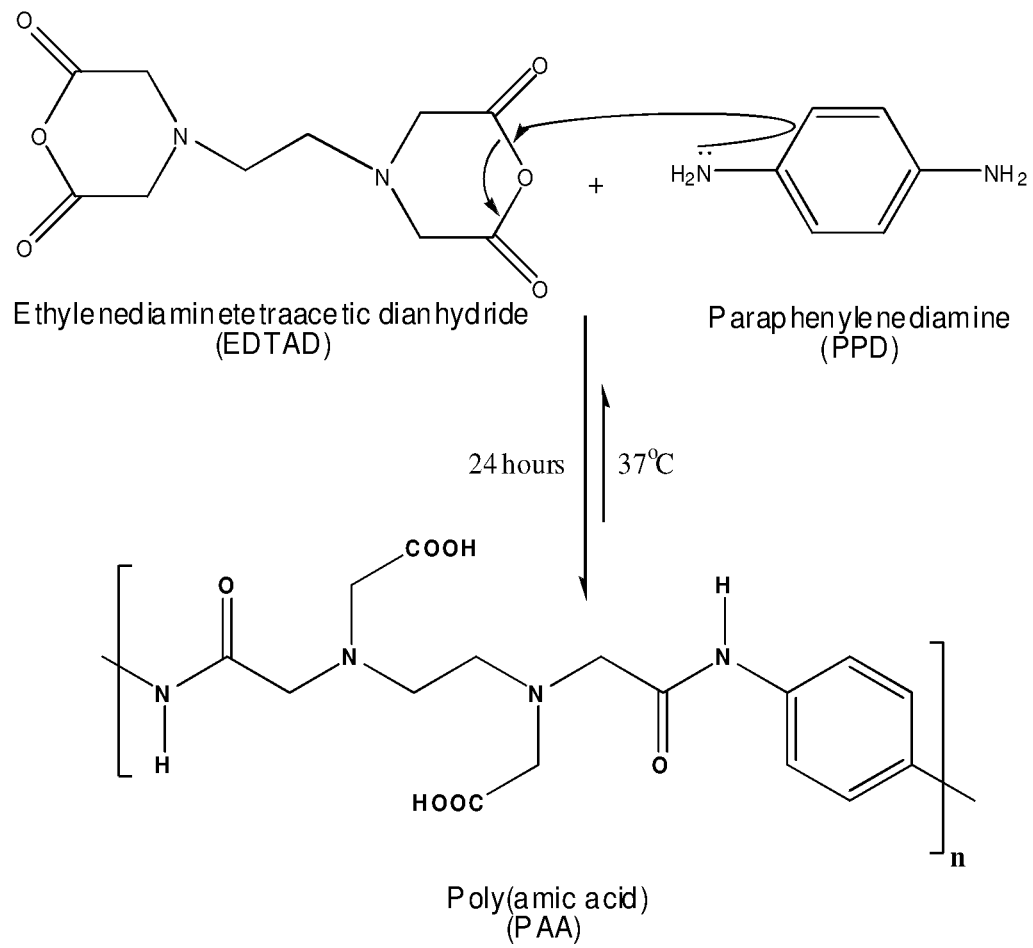
FIG. 1 shows a diagram illustrating the synthesis of poly(amic acid).

FIG. 1 illustrates the preferred poly(amic acid) (PAA) structure, and its synthesis based on the monomers ethylenediaminetetraacetic dianhydride (EDTAD) (a linear dianhydride) and paraphenylenediamine (PPD) (an aromatic diamine).

Figure 2:
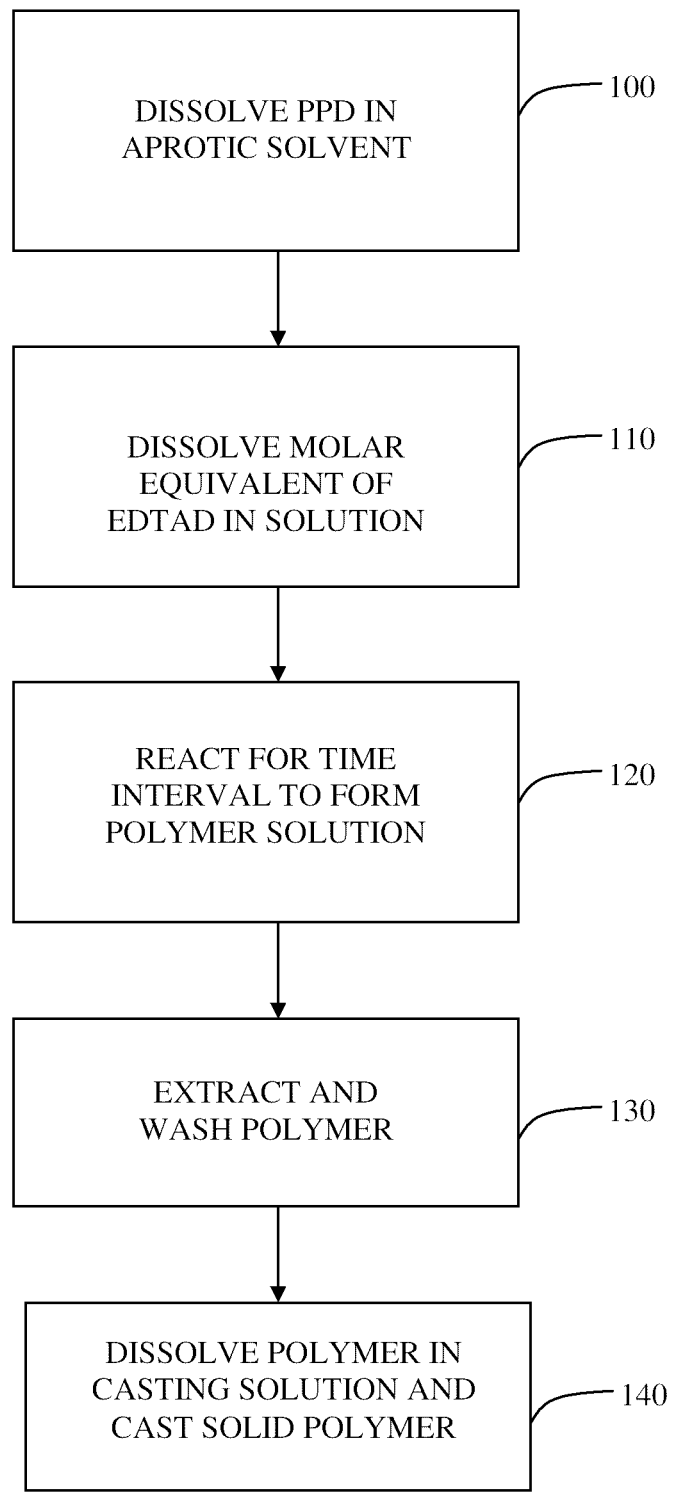
FIG. 2 provides a flow chart illustrating a method of preparing a poly(amic acid).

Referring to FIG. 2, a flow chart is provided that illustrates a method of preparing the PAA shown in FIG. 1. In step 100, PPD is dissolved into an aprotic solvent. The dissolution process is preferably controlled at a fixed temperature, where the fixed temperature is preferably approximately 37° C. In a non-limiting example, the temperature may be controlled using a heater and a water bath. Suitable dissolving means may be employed, such as a stirring bar and a magnetic stirrer. Preferably, the apparatus further comprises a condenser.

In step 110, a molar equivalent quantity of EDTAD is added to and dissolved in the PPD solution, at which point the polymerization reaction is initiated. Without being bound by theory, the polymerization is believed to be initiated through an uncatalyzed mechanism in which the nucleophilic amine from the PPD attacks the carbonyl groups of the cyclic anhydride, as shown in FIG. 1. The polymerization reaction is allowed to proceed for a selected time interval, over which the viscosity of the solution increases. In a preferred embodiment, the time interval is between approximately 24 and 30 hours. During the time interval, the solution temperature is preferably maintained at a controlled value (preferably at within the range of approximately 20 to 45° C., and more preferably at approximately 37° C.). Preferably, the reaction is performed in an inert atmosphere, for example, under nitrogen gas. This may be achieved, for example, by periodically purging the reaction vessel with an inert gas such as nitrogen.

In step 130, the polymer is extracted from solution. Prior to extraction, the synthesized PAA solution may be stored until further use and is preferably stored in a refrigerated environment. PAA polymer may be extracted from solution, for example, by precipitation in cold water, and subsequent filtration, or by solvent evaporation. The extracted PAA is then washed for the removal of residual monomers and oligomers.

A casting solution is then prepared in step 140 by redissolving the extracted PAA in a suitable solvent. The solvent is preferably NMP, and other non-limiting examples of suitable solvents include any of the aforementioned aprotic solvents (DMSO and DMAc). The resulting PAA solution is then cast into a desired shape or surface coating on a substrate. Alternatively, the PAA may be spun into fibers of desired diameter, or formed into a micro- or nanoporous material (preferably suitable for tissue engineering applications), as further described below.

In one non-limiting embodiment, PAA may be cast onto a Teflon mold for forming coatings or solids with smooth surface profiles. Cast PAA is preferably subsequently stored in an environment suitable for the evaporation of residual gases (such as a fume hood). Following the removal of residual gases, the cast PAA is preferably thermally incubated in a controlled thermal environment (such as an oven) for a predetermined time interval in order to remove solvent remaining in the polymer. A preferred time interval for thermal incubation is approximately 3-7 days, and a preferred temperature range is approximately 35-40° C. This step is preferably employed when the PAA is to be used in biomedical applications, where the toxicity of the solvent may be otherwise problematic.

While the process described above recites various ranges for the process parameters, it is to be understood that the process parameters, such as the mixing rate, controlled temperature, and reaction time interval may be varied without departing from the scope of the present embodiments.

The PAA polymer prepared according to the above process exhibits properties that significantly improve over known polymer materials. Advantageously, the poly(amic acid) disclosed in FIG. 1 exhibits the unique property of biocompatibility with cells and cellular growth. As shown in the Examples below, the biocompatibility of the PAA composition disclosed above was assessed in terms of its cell compatibility. To achieve this, primary cultures of porcine radial artery cells (RACs) and descending aorta endothelial cells (ECs) were seeded onto PAA films to measure cell adherence, morphology and proliferation. The observed biocompatibility of the PAA with both cell types underlines its unique biocompatibility and suitability for a wide range of biomedical devices, compositions, and uses.

Accordingly, embodiments of the invention include various biomedical devices and compositions comprising the presently disclosed PAA prepared from the EDTA-PPD monomer combination. In a preferred embodiment, the PAA may be cast as a biomedical implant, or may be coated onto the surface of a biomedical implant. In a non-limiting example, the surface of a biomedical implant such as a coronary stent may be coated with the presently disclosed PAA to provide an implant having a biocompatible surface.

The implant may comprise a permanent replacement, or a temporary replacement. In a preferred embodiment, the PAA may be degraded enzymatically via the amide linkage. This is an attractive feature for biomedical applications and may be considered for a wide range of applications, including, but not limited to, a tissue engineering scaffold material, a controlled release/drug delivery vehicle and/or a temporary replacement medical device material.

The functional groups present in the structure shown in FIG. 1 allow for tailoring of the material properties of the PAA for biomedical uses. Possessing two functional groups of a carboxylic acid and an amide per monomer unit, PAA can provide for covalent attachment to bioactives molecule or agents and/or ligands. Non-limiting examples of such bioactives and/or cell specific ligands include drugs, peptides, sugars, and cell-specific ligands. The conjugation of bioactive agents can be accomplished either in a homogeneous solution or after the PAA has been converted into the desired shape for a particular application.

In a preferred embodiment, one or more bioactive agents are conjugated to the PAA in order to provide delivery of the bioactive agents to targeted sites and/or cells. Such bioactive agents may also be conjugated to the PAA to provide a controlled-release drug delivery vehicle. An example of a drug that can be beneficially conjugated is the well known anticancer drug doxorubicin. Conjugation to PAA of bioactives may prevent their premature enzymatic degradation and enhance their circulation time, which can be therapeutically advantageous. This may also improve the solubility and bioavailability of the drug.

In another embodiment, PAA as described above may provide a suitable material for tissue engineering. PAA can be transformed into a porous or fibrillar scaffold on the micrometer to nanometer scale, which can recruit cells after implantation. Such structures are described in M. M. Stevens and J. H. George, Science 310, 1135 (2005), K. M. Woo, V. J. Chen, P. X. Ma, J. Biomed. Mater. Res. A 67, 531 (2003), F. Yang, R. Murugan, S., Ramakrishna, X. Wang, Y.-X. Ma, S. Wang, Biomaterials 25, 1891 (2004); Mina Mekhail, Kenneth Kar Ho Wong, Donna Teresa Padavan, Yan Wu, David B. O'Gorman and Wankei Wan, Journal of Biomaterials Science (2011) DOI:10.1163/092050610X538209, which are incorporated herein by reference in their entirety. Alternatively, PAA scaffolds can also be seeded with the desired cells and precultured before implantation. PAA has the advantage of sustaining both approaches. Bioactivity can be further enhanced by making use of the functional groups present as stated in the paragraph above.

The following examples are presented to enable those skilled in the art to understand and to practice the present invention. They should not be considered as a limitation on the scope of the invention, but merely as being illustrative and representative thereof.

EXAMPLES

Example 1

Synthesis of PAA Films

Samples of the PAA polymer were prepared using the dianhydride monomer EDTAD (Sigma Aldrich, Oakville, Canada) and the diamine monomer PPD (Thermo Fisher Scientific Company, Acros, Belgium). The EDTAD was received sealed under nitrogen to avoid moisture, had a purity of 98% and was used immediately upon breaking the seal. The PPD was of high purity and was used as received. All organic solvents; N-methyl-2-pyrrolidone (NMP), N,N dimethylformamide (DMF), dimethyl sulfoxide (DMSO) and N,N-dimethylacetamide (DMAc) were also obtained from Sigma Aldrich in sealed vials and either used directly after opening or were dried over molecular sieves having a nominal pore diameter of 3 Å and filtered prior to use. The chemicals needed for preparing the Phosphate Buffered Solution (PBS) [sodium chloride (NaCl), potassium chloride (KCl), disodium hydrogen phosphate (Na$_2$HPO$_4$) and potassium dihydrogen phosphate (KH$_2$PO$_4$)] were also purchased from Fisher Scientific.

In a typical polymerization, PAA polymers comprising amide and carboxylic acid groups were synthesized via ring opening polymerization using a dianhydride and a diamine as monomers in various aprotic solvents such as DMF, DMAc, DMSO and NMP (Scheme 1). A 1 mol equivalent of PPD was placed into a 100 mL, three-necked round bottomed flask and dissolved in an aprotic solvent at a fixed temperature of 37° C. The apparatus consisted of a condenser, heating element, water bath, stirring bar and magnetic stirrer. A 1 mol equivalent of EDTAD was added to the PPD solution containing PPD and the chosen reaction solvent. Nitrogen gas (N$_2$) was purged periodically throughout the duration of the experiment and the experiment was triplicated for reproducibility. All experiments were conducted for a minimum of 24 hours during which time the viscosity of the polymer's solution increased. The synthesized PAA solution was stored at 4° C. in the refrigerator until further use.

Samples were removed from the refrigerator, precipitated in cold water, filtered over a Buchner funnel and cast on either cover slips or in a Teflon mold to produce smooth, circular, coatings having a diameter of 1.8 mm. Samples were placed in a fumehood overnight to evaporate any residual solvent, and then placed into the vacuum oven of 30° C. for 72 hours. The dried film was removed from the glass cover slip or Teflon mold and rinsed with cold water and placed into the oven for an additional 24 hours.

Samples were prepared in the aforementioned solvents to determine their effect on cell seeding experiments. The polymerization was initiated through an uncatalyzed mechanism in which the nucleophilic amine from the PPD attacked the carbonyl groups of the cyclic anhydride (Scheme 1). Control over polydispersity and quantitative yield is achievable by maintaining a 1:1 stoichiometric monomer molar ratio in which EDTAD is added to a PPD solution, reaction temperature of 37° C. is sustained and reaction time of 24 hours is upheld. The reaction solution became viscous over the course of 24 hours and appeared as a viscous yellowish reddish solution. The PAA polymer was readily soluble in polar aprotic solvents such as DMF, DMSO and NMP but insoluble in aqueous solutions. PAA was isolated and prepared for characterization.

Example 2

Characterization of PAA Films

Attenuated Total Reflectance—Fourier Transform Infrared (ATR-FTIR; Pike Technologies Inc., Madison, Wis.) spectroscopy was used to analyze chemical structure and conformation of the PAA film. Infrared spectra were obtained with a horizontal ATR attachment using a diamond crystal on a Bruker Vector 22 FTIR spectrometer (Milton, ON). Spectra were recorded with 128 signal averaged scans at resolution of 4 cm$^{-1}$ and displayed in absorption mode. All spectra were normalized and smoothed using OPUS-NT 3.1 software to enhance the signal to noise ratio.

Figure 3:
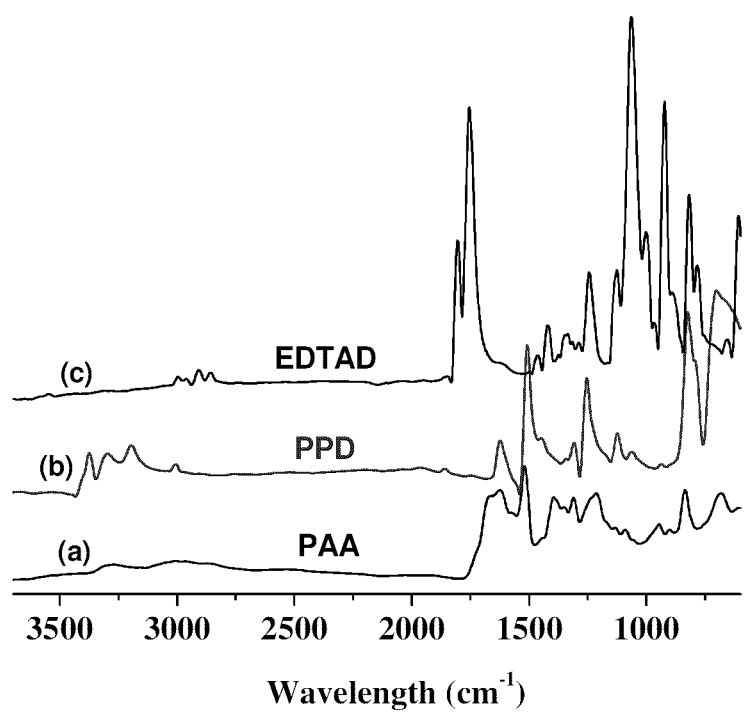
FIG. 3 provides representative ATR-FTIR spectra for (a) poly(amic acid) film, (b) paraphenylenediamine monomer, and (c) ethylenediaminetetraacetic dianhydride monomer.

FTIR spectroscopy analysis was used in the range of 1500-1700 cm$^{-1}$ and 2800-3500 cm$^{-1}$. FIG. 3 shows the representative ATR-FTIR spectra for the PAA film. As anticipated, common bands associated with PAA appeared at approximately 1675 cm$^{-1}$ (amide I) and 1520 cm$^{-1}$ (amide II), corresponding to the stretching vibration of C=O band and combination band of N—H bending and C—N stretching vibration respectively. Additionally, peaks associated with the C=O stretching vibration of the dianhydride bond (1811 cm$^{-1}$ and 1752 cm$^{-1}$) disappeared as would be expected in the presence of a nucleophilic species (diamine) [8]. Similarly, the disappearance of the two well defined peaks linked to the symmetric stretching of the N—H band in the PPD spectra (between 3250 and 3450 cm$^{-1}$), clearly suggests that the primary amines have reacted. The presence of a weak broad peak at 3250 cm$^{-1}$ in the final product represents a secondary amine signifying the N—H band from the amide. There was very little difference in FTIR spectra among all PAA samples. To identify PAAs confirmation, proton and carbon nuclear magnetic resonance was performed.

NMR spectra (Proton Nuclear Magnetic Resonance ($^1$H-NMR) and Carbon Nuclear Magnetic Resonance ($^{13}$C-NMR)) were recorded on an INOVA 600 (Varian, 600 MHz) instrument using deuterated dimethylsulfoxide (d$_6$-DMSO) as the solvent and tetramethylsilane (TMS) as the reference (TMS=0 ppm). The relaxation delay and the angle pulse used for the $^1$H-NMR spectra were 1 second and 45 degrees. The number of scans for $^1$H-NMR and $^{13}$C-NMR were 128 scans and 1024 respectively. ACD Labs Version 11.0 software was used to process NMR data. In the analysis, phasing parameters and baseline points were determined on the first transformed spectrum. Data transformation and peak height measurements were automated and integration was performed manually. Coupling constants and chemical shifts were given in hertz (Hz) and parts per million (ppm), respectively.

Figure 4:
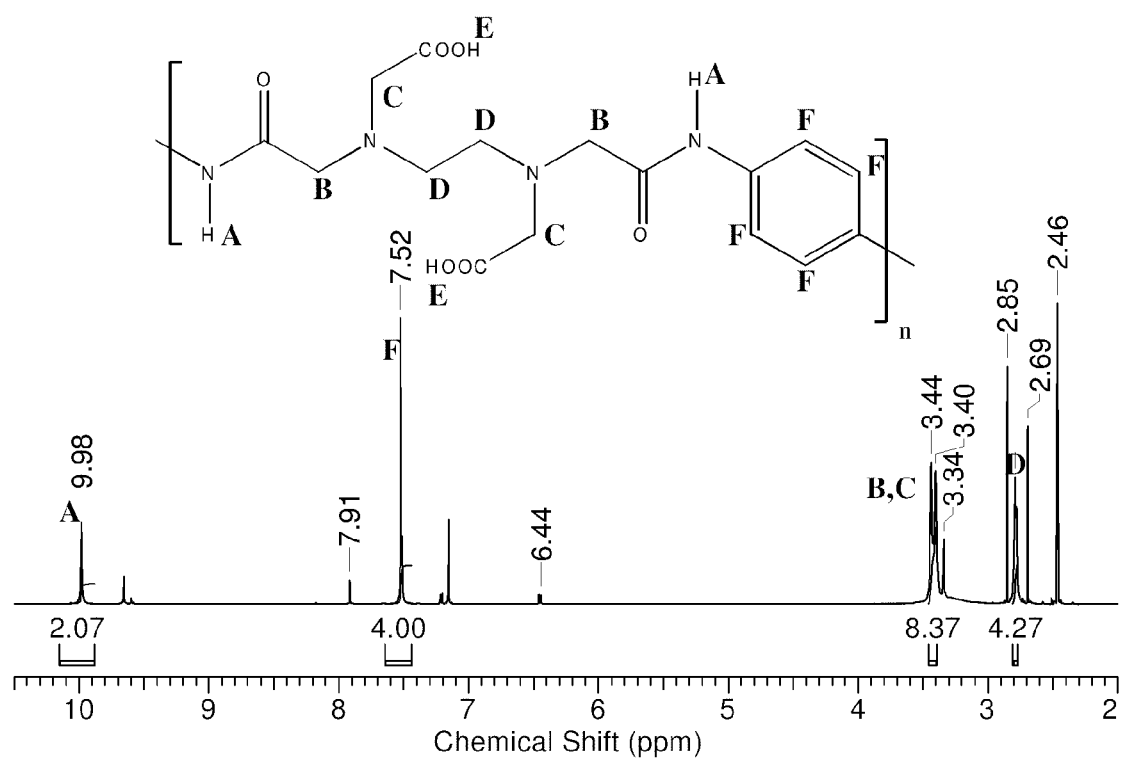
FIG. 4 shows the $^1$H-NMR Spectrum ($d_6$-DMSO) of PAA.

FIG. 4 shows the spectrum of PAA synthesized in DMF and quantified in DMSO-d$_6$. Peaks observed in the $^1$H-NMR spectrum (600 MHz, DMSO-d$_6$, 1 wt %), δ (ppm): 2.69 (s, 3H); 2.79 (2s, 4H labeled 'D'); 2.85 (s, 3H); 3.40-3.45 (m, 8H labeled 'B and C'); 7.49-7.53 (4H, labeled 'F'); 9.98 (s, 2H labeled 'A') confirmed PAA structure. The spectrum was normalized with the aromatic protons from the PPD monomer. Peaks in the range δ 7.54 and δ 6.44 ppm corresponded to the aromatic hydrogens in the backbone of the PAA polymer as well as hydrogen residues from the PPD monomer. The sharp peak at δ 9.98 ppm was attributed to the hydrogens from the amide group. The peak at δ 2.79 ppm signified hydrogens attached to carbons neighbouring nitrogen in the backbone of the PAA polymer. In addition to the nuclear resonances mentioned above, there were five distinct peaks appearing at δ 2.46, δ 2.69, δ 2.85, δ 3.34 and δ 7.91 ppm representing DMSO-d$_6$, methyl group from DMF, another methyl group from DMF, presence of moisture and an N—H proton from DMF respectively. In this particular spectrum, the acid proton was not captured, and is often difficult to capture as a result of deuterium exchange. It was anticipated and observed that the acid hydrogen has a large chemical shift, downfield near δ 12 ppm since it is highly deshielded as a result of its direct attachment to oxygen. The integrals of the peaks at δ 9.98 ppm (amide protons), δ 7.52 ppm (aromatic protons), δ 3.40-δ 3.44 ppm (methylene protons neighbouring an amide or acid) and δ 4.27 ppm (methylene protons off a carbon adjacent to a nitrogen) provided the actual content of the PAA polymer and was consistent with the corresponding number of protons in the repeating unit of PAA. To verify the presence of the acid segment of PAA, $^{13}$C-NMR was performed to identify the carbonyl carbon associated to the acid.

Figure 5:
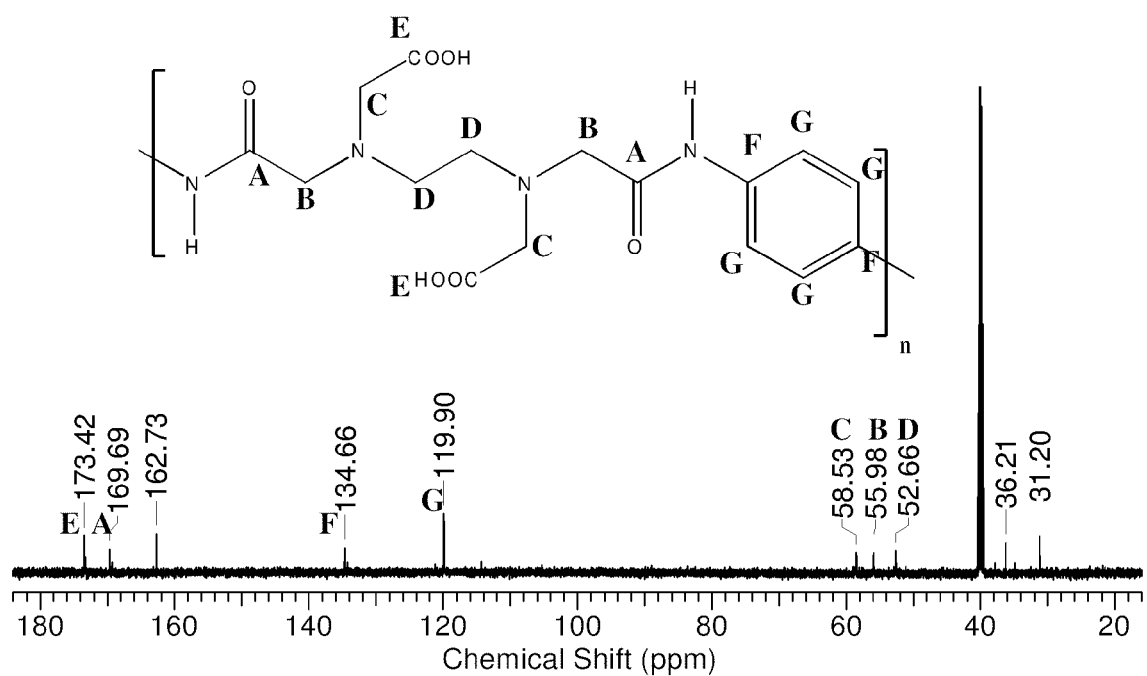
FIG. 5 shows the $^{13}$C-NMR Spectrum ($d_6$-DMSO) of PAA.

FIG. 5 illustrates a characteristic PAA $^{13}$C-NMR spectrum in d$_6$-DMSO displaying typical carbonyl resonances associated with amides and acids between δ 162-δ 174 ppm. The $^{13}$C-NMR spectrum shows three downfield signals at δ 173.42 (labeled 'E'), δ 169.69 (labeled 'A') and δ 162.73 representing the acid carbonyl carbon, the amide carbonyl carbon and the amide carbonyl carbon from the reaction solvent DMF respectively. The spectrum of PAA also shows two comparatively distinct signals at δ 134.66 and δ 119.90 in the aromatic region representing aromatic carbons in the backbone of the PAA polymer as a result of the PPD monomer. A subtle shift of the aromatic carbons in the PAA backbone is evident compared to the PPD monomer (δ 139.34 and δ 115.86). In addition to the solvent peak at δ 40 ppm, five upfield signals at δ 58.53 (labeled 'C'), δ 55.98 (labeled 'C'), δ 52.66 (labeled 'D'), δ 36.21 and δ 31.20 are discrete and denote methylene carbons adjacent to an acid, amide and nitrogen and methyl groups as a result of trace amounts of DMF. $^{13}$C-NMR spectroscopy proved to be a valuable technique in the detailed analysis of PAA.

Dried PAA samples were analyzed on a Perkin-Elmer Pyris 1 DSC instrument. Indium was used as the temperature and enthalpy calibrator. Five mg samples were weighed and fixed in an aluminum pan with lid while an empty pan with lid was used as a reference. The glass transition temperature was examined between 50 and 500° C. at a heating rate of 10° C./min using nitrogen as a purge gas at 40 ml/min. All samples were held at 500° C. for 5 minutes and then cooled at a rate of 10° C./min. PAA thermograms were analyzed to determine the decomposition temperature using Pyris 1 Version 3.01 software.

Figure 6:
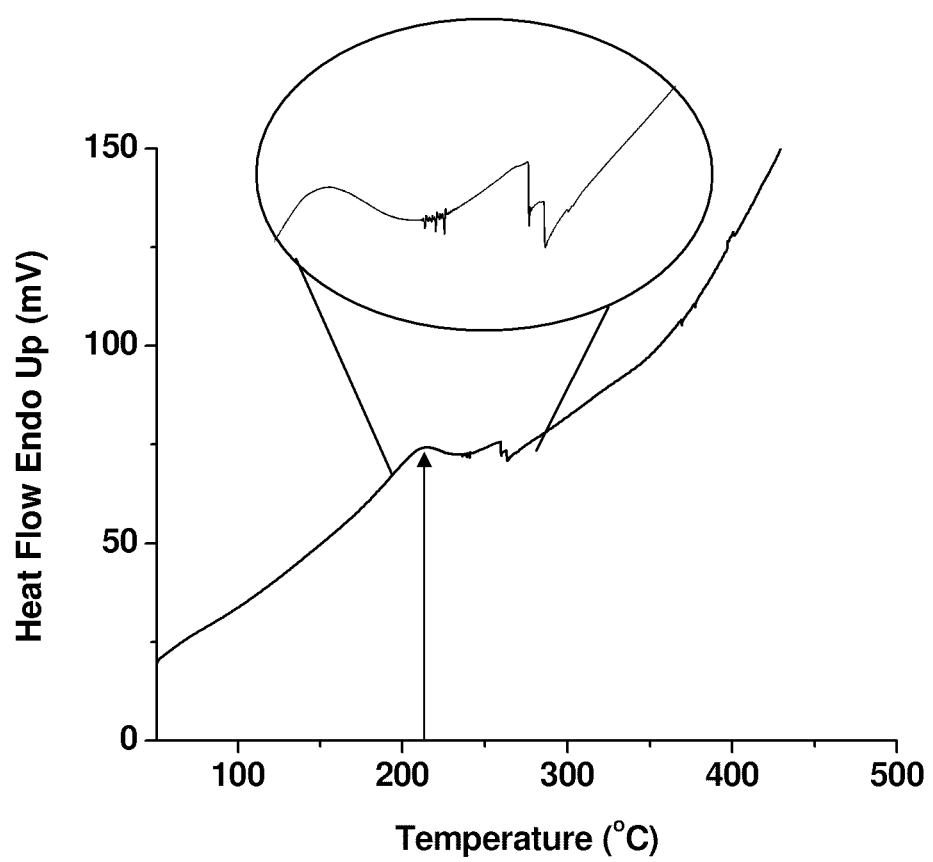
FIG. 6 shows the DSC Thermogram of PAA.

The endothermic peak of PAA cast from DMF solution is seen in FIG. 6 and appears around 214° C. The broad peak represents the decomposition temperature of PAA and the initiation of PAAs cyclization prior to its conversion into polyimide. Glass transition temperature was not detectable in any of the thermograms.

PAA samples were mounted on a carbon paper and examined and photographed using an SEM and an EDX instrument. Measurements of the product PAA films were obtained using the LEO-Zeiss 1540XB FIB/SEM which was equipped with an EDX Si-detector (Oxford Instruments). A low accelerating voltage of 8 kV was used to minimize the surface charging effect of PAA with the sample tilted at 45° to the incident electron beam.

The presence of three large intensities; carbon ($C_{1s}$=0.28 KeV), oxygen ($O_{1s}$=0.52 KeV) and nitrogen ($N_{1s}$=0.39 KeV) on the EDX survey scan were clearly evident. Table 1 shows is a non-conductive polymer, a low accelerating voltage of 8 kV was used to minimize the surface charging effect instead of applying a carbon or gold coating which might compromise the accuracy of the elemental analysis.

TABLE 1

Elemental Analysis

| Element | Experimental Values Atomic (%) PAA 1 | Experimental Values Atomic (%) PAA 2 | Experimental Values Atomic (%) PAA 3 | Theoretical Values Atomic (%) |
|---|---|---|---|---|
| Carbon | 55.80 | 56.25 | 58.28 | 55.84 |
| Oxygen | 24.07 | 23.19 | 22.92 | 27.88 |
| Nitrogen | 20.13 | 20.56 | 18.80 | 16.28 |
| Total | 100 | 100 | 100 | 100 |

The molecular weights; number average molecular weight ($M_n$) and weight average molecular weight ($M_w$), and polydispersity index (PDI) of the PAA samples were obtained by gel permeation chromatography (GPC). GPC was conducted in hexafluoroisopropanol (HFIP) (0.75 mL/min) at 40° C. using a Viscotek Model 302-050 chromatography system equipped with a refractive index, light scattering and viscosity detectors and three columns (2, PolyAnalytik HFIP-604 and 1, PolyAnalytik HFIP-606) in series. NIST-traceable polymethylmethacrylate (Polyanalytick PMMA 98K) standards were used for calibration. PAA samples were diluted to 6 mg/mL in DMF and injected three times per sample at an injection volume of 100 μL.

TABLE 2

Summary of GPC Data

| | Molar Ratio | $M_n$ (g/mol) | $M_w$ (g/mol) | PDI | Temp (°C.) | M [ ] (mols/L) | Reaction Time (hours) | Solvent |
|---|---|---|---|---|---|---|---|---|
| S1 | 1:1 | 101,381 | 144,290 | 1.423 | 36.6 | 0.25 | 24.0 | DMAc |
| S2 | 1:1 | 123,254 | 180,455 | 1.464 | 37.0 | 0.25 | 24.5 | DMF |
| S3 | 1:1 | 190,398 | 239,176 | 1.256 | 37.2 | 0.25 | 25.5 | NMP |

$^a$The molar ratio represents [diamine]$_0$/[dianhydride]$_0$,
$M_n$ = Number Average Molecular Weight,
$M_w$ = Weight Average Molecular Weight,
PDI = Polydisersity Index = $M_w/M_n$,
Temp = Temperature,
M [ ] = Monomer Concentration the experimental relative amounts of carbon, oxygen and nitrogen from three PAA samples and compares them to their theoretical values based on the repeating unit of PAA. The average experimental atomic % for the three polymers samples (% Carbon=56.8±1.3, % Oxygen=23.4±0.6 and % Nitrogen=18.8±0.9) were comparable and relatively close to the theoretical values. However, the % composition for both oxygen and nitrogen were statistically significant (t-test; p<0.05) most probably due to radiation damage by the electron beam, surface charging of the samples and overlapping intensities between the nitrogen and carbon peaks. Since PAA The ring opening polymerization of EDTAD with PPD led to a viscous yellowish/red solution with high yield and high number average molecular weights ($M_n$) ranging from 100,000 to 200,000 g/mol. Table 2 displays a summary of the data obtained from GPC. The $M_n$ of PAA seemed to increase linearly with increasing temperature and reaction time. From table 2, it was concluded that all PAA samples synthesized had relatively narrow molecular distributions with polydispersity index (PDI)<1.45 suggesting that polymerizations proceeded in a controlled fashion. PAA containing acid and amide functional groups were successfully synthesized at this point and characterized using a variety of analytical tools: FTIR, $^1$H-NMR, $^{13}$C-NMR, DSC, EDX and GPC. As a result, chemical structure and physical properties were established. PAA has a high molecular weight and exhibits good thermal stability with a decomposition temperature of 214° C. To assess the materials biocompatibility, the latter part of this paper will focus on cell adhesion, cell proliferation and cell toxicity.

Example 3

Assessment of PAA Biocompatibility

Primary cultures of porcine radial artery cells (RACs) and porcine descending aorta endothelial cells (ECs) were isolated as previously described [5, 6]. Radial artery cells were maintained in Medium 199 (M199) supplemented with 10% fetal bovine serum (FBS) and 1% Penicillin/Streptomycin (Invitrogen Canada, Burlington, ON). ECs were maintained in endothelial growth medium (EGM) with 5% FBS, 1% Penicillin/Streptomycin and a bullet kit containing rhEGF, rhFGF-B, VEGF, R$^3$-IGF-1, gentamicin/amphotericin, hydrocortisone, and ascorbic acid (Lonza Canada Inc., Shawinigan, QC). All cells were maintained at 37° C. under humidified gas mixture of 95% air/5% $CO_2$. RACs (passages four to six) and ECs (passages three to five) were independently seeded onto PAA coated cover slips at an initial cell density of 7,000 cells/cm$^2$. Uncoated cover slips were seeded at the same density to serve as time-matched controls. Cell growth and adhesion was examined at 4, 8, and 24 hours and cell proliferation was quantified at 24, 48 and 72 hours.

The number of adherent cells was measured using phase contrast microscopy at 10× magnification. Phase-contrast microscopy was performed on live cells using an Olympus CK40 inverted microscope (Olympus Canada Inc., Markham, ON) with a Sony 3CCD Color Video Camera (Sony of Canada Ltd., Toronto, ON) and Northern Eclipse Version 7.0 imaging software (Empix Imaging Inc., Mississauga, ON). Ten random frames per sample were imaged to analyze proliferation over time. For each frame, the number of adherent cells was counted and cell counts were averaged to generate cell density values at 24, 48, and 72 hours. Studies were preformed in triplicate to confirm reproducibility. Following phase-contrast microscopy, cells were fixed in 10% formalin for immunolabeling.

Radial artery cell-seeded cover slips were stained with monoclonal mouse anti-smooth muscle α-actin (SMA)-Cy3 conjugated IgG2a primary (clone 1A4, 1:50) (Chemicon, Temecula, Calif.). Endothelial cell-seeded cover slips were stained with polyclonal rabbit anti-Human Von Willebrand Factor primary IgG (A0082, 1:50) (Dako Canada Inc., Mississauga, ON) and AlexaFluor® 488 goat anti-rabbit IgG secondary (1:200) (Invitrogen Molecular Probes, Eugene, Oreg.). Nuclei were labeled with Hoechst 33342. Immunolabeled cover slips were analyzed with a Zeiss LSM 410 laser-scanning confocal microscope system and LSM-PC imaging software (Carl Zeiss Canada Ltd., Toronto, ON).

Cell viability was evaluated using the WST-1 assay. Briefly, ECs and RACs were seeded into a polystyrene 96-well flat-bottom plate coated with PAA (50 µL polymer solution placed in 96-well plate and dried in a fumehood for 24 hours) or uncoated (control) in triplicate for each polymer sample at a density of 5000 cells/well. Cells were incubated for 24, 48, 72 or 96 hours and viability was measured using the WST-1 assay. A solution of 10 µL/well of WST-1/ECS was added and the optimal incubation time for this experimental setup was determined as 2 hours. Quantitative measurements were obtained on a multi-well spectrophotometer (microplate reader) by measuring the absorbance of the treated and untreated samples at 450 nm with background subtraction (reference wavelength) at 600 nm [7].

Data analysis was carried out using OriginPro Version 8.0 (OriginLab software, Northampton, Mass.) statistical software package. Data was analyzed by either a one-way analysis of variance (ANOVA) or student's t test. In all instances, a p value of less than 0.05 was considered significant.

Assessing polymeric materials for cell compatibility is necessary prior to their application in the biomedical field. The following subsections provide preliminary cell compatibility assessment of PAA using an in vitro cultured cell based system consisting of primary porcine radial artery cells (RACs) and descending aorta endothelial cells (ECs).

Figure 7A:
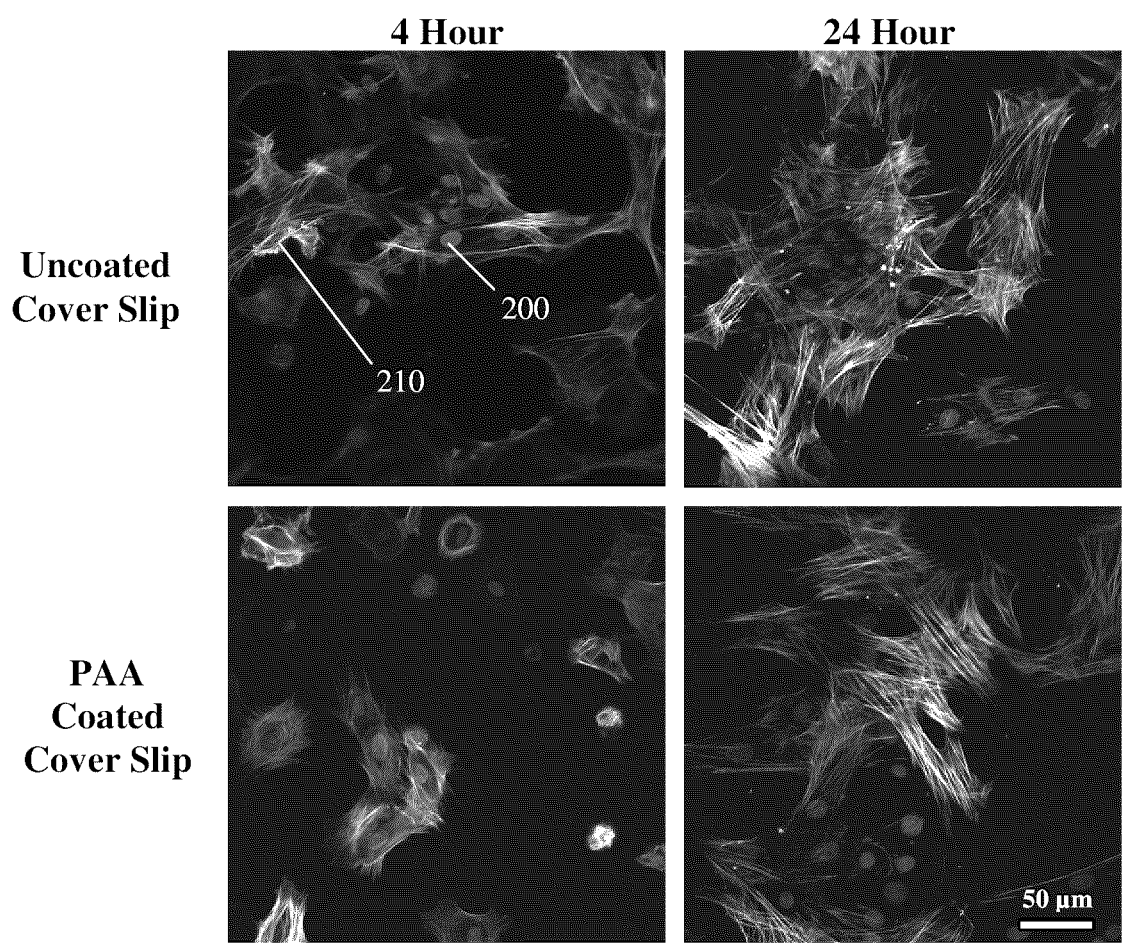
FIG. 7(a) provides confocal images of porcine radial artery cells (RAC)s at 4 and 24 hours on an uncoated (control) and PAA coated cover slips.
Figure 7B:
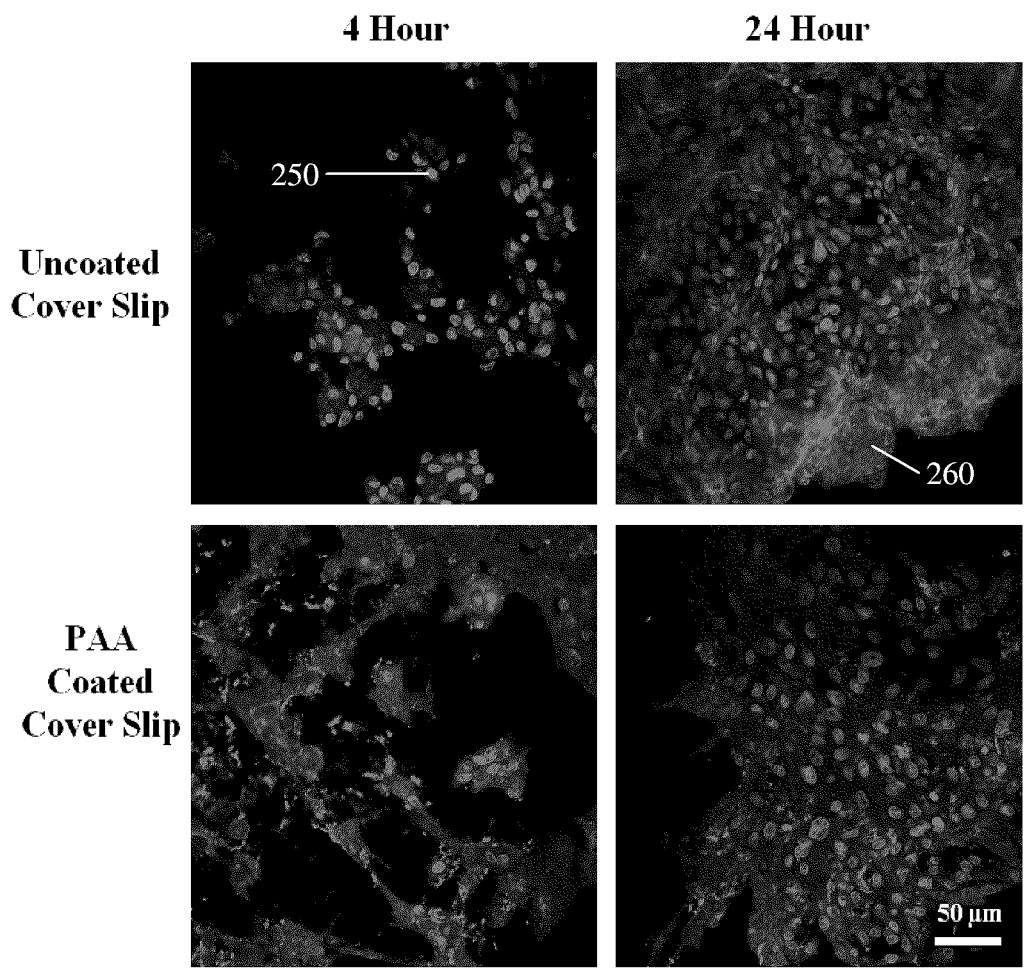
FIG. 7(b) provides confocal images of aorta endothelial cells (EC)s at 4 and 24 hours on an uncoated (control) and PAA coated cover slips.

RACs and ECs were seeded independently onto PAA coated and uncoated (control) glass cover slips having a diameter of 1.8 mm at a cell density of 7000 cells/cm$^2$. Cell adhesion and morphology was examined at 4, 8 and 24 hours. FIG. 7a and FIG. 7b display confocal images of RACs and ECs at 4 and 24 hours respectively. At 4 hours, there was a distinct difference between both cell types and their respective controls. FIG. 7a (n=8) clearly displays the differences in cell morphology at 4 hours between the coated and uncoated cover slips. The RACs, identified by their nuclei 200 and α-actin cytoskeleton 210 on the uncoated cover slips, adhered at 4 hours and began to extend cellular processes. In contrast, the RACs seeded on the PAA coated cover slips at the same time point appeared round in shape with an uneven cellular border. Minimal cell processes were visible. However, 24 hours later, cellular processes were observed from RACs on both the uncoated and coated cover slips and the RACs exhibited the formation of cellular contacts in a similar manner.

Unlike RACs, ECs formed a confluent layer. FIG. 7b (n=4), displays confocal images of ECs (nuclei are shown at 250 and Von Willibrand factor, a cytoplasmic protein, is shown at 260) at 4 and 24 hours. At the 4 hour time point, ECs seeded on the PAA coated cover slips adhered and cellular processes were observed to extend toward neighbouring cells. In contrast, the ECs on the uncoated cover slips at 4 hours appeared clustered and rounded with no evidence of cytoplasmic extension. However by 24 hours, in a manner similar to the RACs, the ECs had normal morphology on both the coated and uncoated cover slips. While the ECs exhibited growth at 24 hours, confluence was not reached. Preliminary trials also indicated a greater number of ECs on the uncoated cover slips than on the PAA coated cover slips.

Cytotoxicity of the PAA films were initially investigated by direct observation of the RACs and ECs on an inverted microscope, and cell viability was determined by conducting a WST-1 assay. Briefly, WST-1 is a tetrazolium salt which is converted into a soluble form of formazan by cellular mitochondrial dehydrogenases. As the number of viable cells increased, the overall activity increased, leading to an increase in the amount of formazan dye formed and readily quantified by spectrophotometry. The spectrophotometer (plate reader) measures absorbance of the released dye and these values can be used as a quantitative indication of cell viability.

Figure 8A:
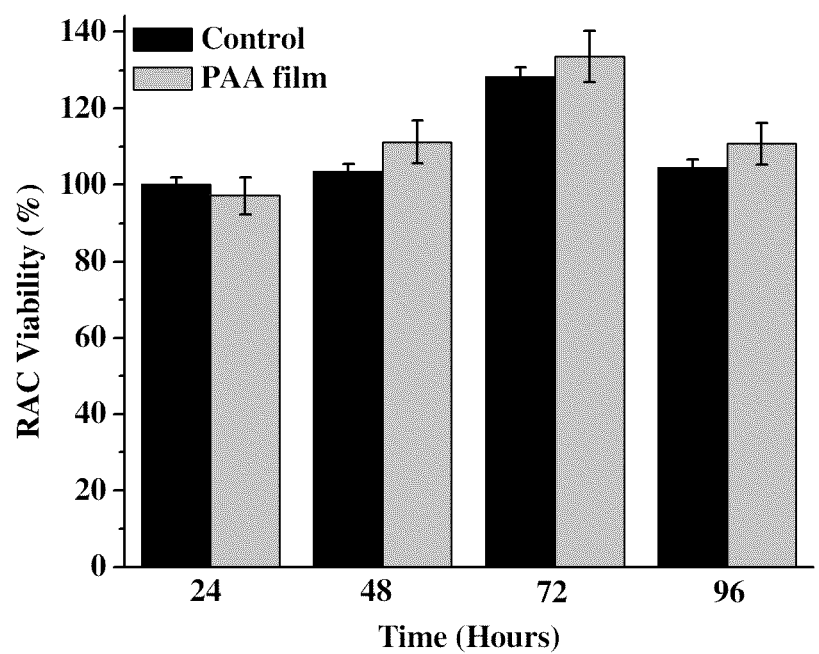
FIG. 8(a) plots the percentage of RAC viability determined by the WST-1 assay on PAA films after 96 hours of incubation.
Figure 8B:
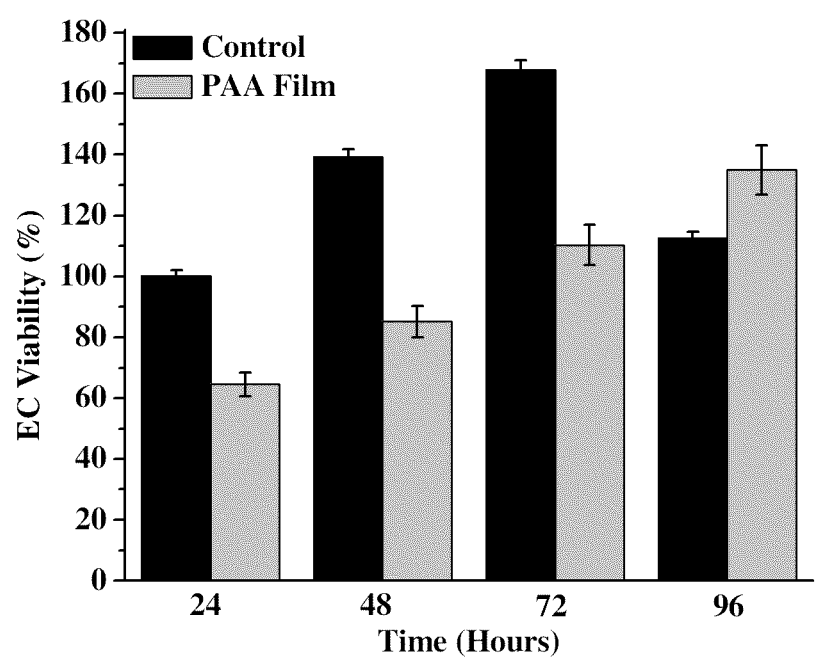
FIG. 8(b) plots the percentage of EC viability determined by the WST-1 assay on PAA films after 96 hours of incubation.

FIGS. 8a (n=4) and 8b (n=4) display the viability results for both RACs and ECs respectively. The results displayed at each time point are presented as a percentage of the control (a polystyrene 96-well containing cells and culture medium) which is rated as 100% at 24 hours. Both RACs and ECs were viable after contacting the PAA films for the duration of 96 hours, as was anticipated from the adhesion studies. These results corroborated observations seen under the inverted microscope as well. FIG. 8a clearly shows the RACs as being viable. The observation of cell adhesion by microscopy confirmed cell viability on PAA and results were very similar to the controls. At some time points (48 hour and 72 hours) the cell growth on PAA was higher than on the control surfaces. Unlike the RACs, ECs growth (viability) was slowed on PAA for the first 3 days (FIG. 8b) and results differed significantly ($p<0.05$) compared to the controls on each day but not between trials. Between 72 hours and 96 hours, a sudden decline in EC growth was apparent on the control. This was likely due to aging media and the consumption of growth factors. Control cells reached confluence before 96 hours whereas, the cells seeded on PAA continued to increase and almost doubled in number compared to the first day of seeding. Microscopy once again corroborated these trends. The WST-1 assay was reproducible and clearly indicated that PAA does not have a toxic effect on the cells after 96 hours of incubation. In addition, it is important to note that hydrolysis of the amide bond in the PAA backbone will not occur in such a short time frame of the experiment and would not a contributing factor in the viability studies. There is no measurable degradation across 10 days (data not shown). Since little to no toxicity and successful cell adhesion was observed with both cell types, cell compatibility could then be assessed to investigate their proliferative nature on the PAA films.

Figure 9:
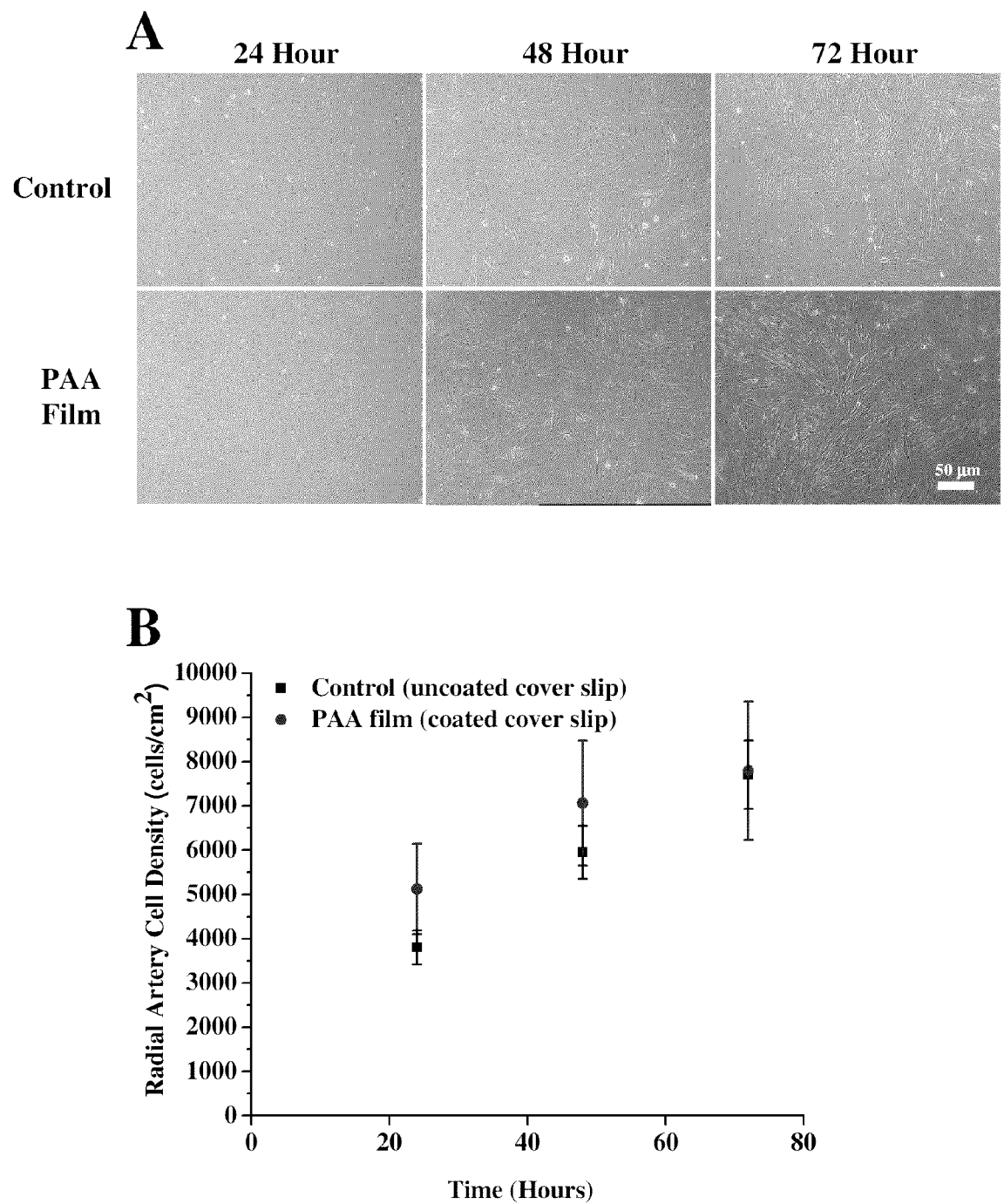
FIG. 9(a) shows phase contrast microscopy images of RACs seeded on control and on PAA films at 24, 48 and 72 hours, and FIG. 9(b) plots RAC proliferation measured by the number of adherent cells on coated and uncoated cover slips at 24, 48 and 72 hours.
Figure 10:
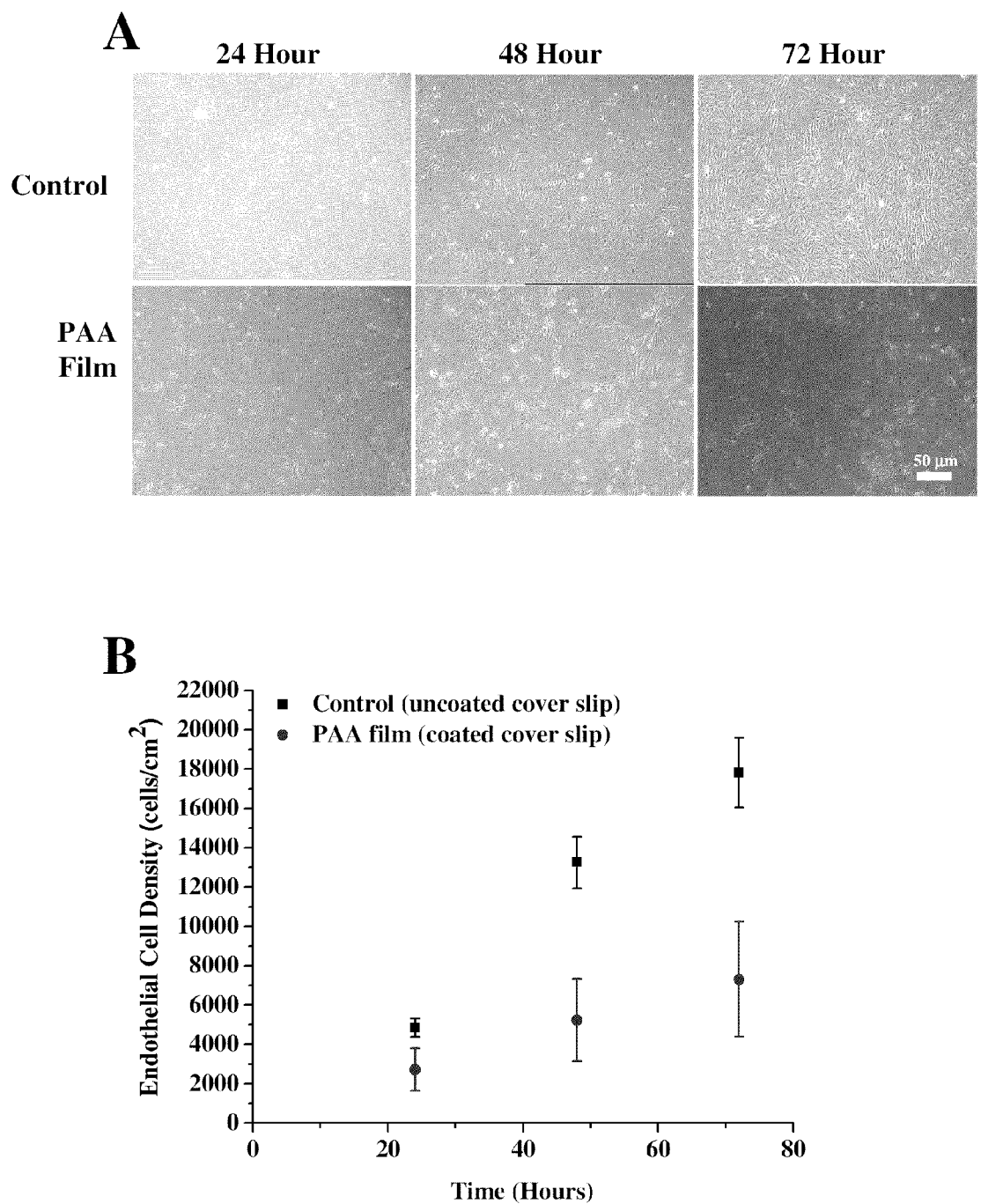
FIG. 10(a) provides phase contrast microscopy images of ECs seeded on control and on PAA films at 24, 48 and 72 hours, and FIG. 10(b) plots EC proliferation measured by the number of adherent cells on coated and uncoated cover slips at 24, 48 and 72 hours.

Since viability studies showed confluence was reached after 72 hours, it was decided that preliminary proliferation studies would run for 3 days (72 hours). FIG. 9a (n=8), FIG. 9b (n=8), FIG. 10a (n=4) and FIG. 10b (n=4) display the proliferation results for RACs and ECs respectively. The rather low contrast of these uncorrected images was most likely due in part to the scattering of the incident light by PAA. FIG. 9a and FIG. 9b clearly showed RACs seeded on PAA adhered, spread and proliferated at an equivalent rate compared to the control. The number of adherent cells measured 72 hours after cell seeding was 7800±1560 cells/cm$^2$ for the PAA coated cover slips and 7700±770 cells/cm$^2$ for the control. There was no statistical difference in the cellular proliferation rates between the control and the PAA coated cover slips. Similar to the RACs, ECs seeded on PAA adhered, spread and proliferated. However, the rate of proliferation was not comparable to the controls. FIG. 10a and FIG. 10b clearly show the statistical difference ($p<0.05$) between ECs seeded on cover slips versus ECs seeded on PAA coated cover slips at each time point. Unlike the RACs, ECs seeded on the control almost quadrupled in number by 72 hours whereas ECs seeded on PAA tripled in number at the same time point. The major noticeable difference was the amount of EC proliferation. At the 72 hour time point, the number of adherent cells measured after cell seeding was 7300±2920 cells/cm$^2$ for the PAA coated cover slips and 17800±1780 cells/cm$^2$ for the control. Despite these statistically significant differences, ECs proliferated on the PAA films and preserved their phenotype for up to 72 hours. Overall, the PAA coating did not affect RAC and EC cell morphology when compared to uncoated controls.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. R. Langer and D. A. Tirrell, *Nature* 428, 487 (2004).
2. X. Jiang, E. B. Vogel, M. R. Smith and G. L. Baker, *Macromolecules*, 41, 1937 (2008).
3. A. A. Ignatius and L. E. Claes, *Biomaterials* 17, 831 (1996).
4. M. Hakkarainen, A. Hoglund, K. Odelius and A. C. Albertsson, *Journal of the American Chemical Society* 129, 6308 (2007).
5. D. E. Johnston, D. R. Boughner, M. Cimini and K. A. Rogers, *J Biomed Mater Res A*, 78A, 383 (2006).
6. K. A. Rogers, P. Boden, V. I. Kalnins and A. I. Gotlieb, *Cell and Tissue Research*, 243, 223 (1986).
7. Millipore, WST-1 Cell Proliferation Assay, http://www.millipore.com/cellbiology/cb3/wst-1 (August, 2009)
8. D. L. Pavia, *Introduction to spectroscopy*, Brooks/Cole, Cengage Learning, Belmont, Calif. 2009.

Therefore what is claimed is:

1. A poly(amic acid) polymer of repeating units of the following formula:

2. The polymer according to claim 1 further comprising a conjugated bioactive moiety, wherein said bioactive moiety is conjugated to one or more of an amide group and a carboxylic group.

3. The polymer according to claim 2 wherein said bioactive moiety is one of drugs, peptides, sugars, and cell-specific ligands.

4. A biomedical implant comprising:
   a substrate; and
   a biocompatible layer coating a surface of said substrate; wherein said biocompatible layer comprises a poly(amic acid) according to claim 1.

5. A biomedical implant comprising a biocompatible poly(amic acid) according to claim 1.

6. A tissue engineering scaffold comprising a biocompatible poly(amic acid) according to claim 1.

7. A controlled release drug delivery vehicle comprising a biocompatible poly(amic acid) according to claim 1.

8. A cellular growth substrate material comprising a biocompatible poly(amic acid) according to claim 1.

9. A process for preparing a poly(amic acid) comprising the steps of:
   forming a solution comprising a quantity of ethylenediaminetetraacetic dianhydride in an aprotic solvent;
   adding to said solution a quantity of paraphenylenediamine, wherein a molar quantity of said paraphenylenediamine is approximately equal to a molar quantity of said ethylenediaminetetraacetic dianhydride; and
   reacting said ethylenediaminetetraacetic dianhydride with said paraphenylenediamine to form a polymer solution of poly(amic acid).

10. The process according to claim 9 wherein said step of reacting said ethylenediaminetetraacetic dianhydride with said paraphenylenediamine to form a polymer solution of poly(amic acid) is performed while maintaining a temperature of said solution for a selected time interval.

11. The process according to claim 10 wherein said temperature is maintained within a range of approximately 20 degrees Celsius to 45 degrees Celsius.

12. The process according to claim 9 wherein said step of reacting said ethylenediaminetetraacetic dianhydride with said paraphenylenediamine to form a polymer solution of poly(amic acid) is performed in a substantially inert atmosphere.

13. The process according to claim 9 wherein said aprotic solvent is one of N-methyl-2-pyrrolidone (NMP), N,N dimethylformamide (DMF), dimethyl sulfoxide (DMSO) and N,N-dimethylacetamide (DMAc).

14. The process according to claim 9 further comprising the step of extracting said poly(amic acid) from said polymer solution.

15. The process according to claim 14 wherein said step of extracting said poly(amic acid) comprises precipitating said poly(amic acid) from said polymer solution and filtering said solution to obtain said poly(amic acid).

16. The process according to claim 14 wherein said step of extracting said poly(amic acid) comprises performing a solvent evaporation step.

17. The process according to claim 14 further comprising the steps of:
 forming a casting solution by dissolving said extracted poly(amic acid) in a solvent;
 casting said poly(amic acid) onto a substrate; and
 drying said poly(amic acid) to obtain a solid.

18. The process according to claim 17 further comprising the step of storing said solid in an environment suitable for removal of residual gases.

19. The process according to claim 17 further comprising the step of thermally incubating said solid for a pre-defined time interval at a temperature suitable for removal of solvent remaining in said solid.

20. The process according to claim 17 wherein said substrate comprises a mold, and wherein said process further comprises the step of separating said solid from said mold.

21. The process according to claim 17 further wherein said substrate comprises a surface of a biomedical implant, and wherein said solid comprises a poly(amic acid) layer coated onto said biomedical implant.

22. The process according to claim 21 wherein said biomedical implant comprises a coronary stent.

23. The process according to claim 21 wherein said biomedical implant comprises a tissue engineering scaffold.

24. The process according to claim 23 further comprising the steps of:
 seeding said poly(amic acid) layer with adherent cells; and
 culturing said adherent cells.

25. The process according to claim 21 further comprising, after having implanted said biomedical implant, the step of enzymatically degrading said poly(amic acid).

26. The process according to claim 9 further comprising the step of conjugating a bioactive moiety to one or more of an amide group and a carboxylic group of said poly(amic acid).

27. The process according to claim 26 wherein said step of conjugating said bioactive moiety is performed prior to extracting said poly(amic acid).

28. A poly(amic acid) polymer prepared by the steps comprising:
 forming a solution comprising a quantity of ethylenediaminetetraacetic dianhydride in an aprotic solvent;
 adding to said solution a quantity of paraphenylenediamine, wherein a molar quantity of said paraphenylenediamine is approximately equal to a molar quantity of said ethylenediaminetetraacetic dianhydride;
 reacting said ethylenediaminetetraacetic dianhydride with said paraphenylenediamine to form a polymer solution of poly(amic acid).

\* \* \* \* \*